United States Patent [19]

Barker

[11] Patent Number: 4,476,877
[45] Date of Patent: Oct. 16, 1984

[54] FLUID TEMPERATURE SENSOR

[75] Inventor: John M. Barker, Port Hueneme, Calif.

[73] Assignee: Gould Inc., Rolling Meadows, Ill.

[21] Appl. No.: 408,080

[22] Filed: Aug. 16, 1982

[51] Int. Cl.³ .............................................. A61B 5/02
[52] U.S. Cl. .................................... 128/736; 128/692; 604/53
[58] Field of Search ............................ 128/691–692, 128/736, 713; 73/204; 604/52–53

[56] References Cited

U.S. PATENT DOCUMENTS

| 2,816,997 | 12/1957 | Conrad | 128/736 X |
|---|---|---|---|
| 3,446,073 | 5/1969 | Auphan et al. | 128/692 |
| 3,511,095 | 5/1970 | Grissom et al. | 128/736 X |
| 3,545,428 | 12/1970 | Webster, Jr. | 128/692 |
| 3,561,266 | 2/1971 | Auphan et al. | 73/204 |
| 3,595,079 | 7/1971 | Grahn | 73/204 |
| 3,620,207 | 11/1971 | Sinclair | 73/204 X |
| 3,645,133 | 2/1972 | Simeth et al. | 73/204 |
| 3,703,892 | 11/1972 | Meyers | 128/736 |
| 3,726,269 | 4/1973 | Webster, Jr. | 73/204 X |
| 3,833,115 | 9/1974 | Schapker | 128/736 X |
| 3,915,155 | 10/1975 | Jacobson et al. | 128/692 |
| 4,153,048 | 5/1979 | Magrini | 128/692 |
| 4,317,453 | 3/1982 | Heim et al. | 128/724 X |
| 4,936,211 | 7/1977 | Veth et al. | 128/666 |

FOREIGN PATENT DOCUMENTS 721078 3/1980 U.S.S.R. ............................ 128/692

Primary Examiner—Lee S. Cohen
Assistant Examiner—Angela D. Sykes

[57] ABSTRACT

A temperature sensing device for use in a fluid flow system for accurately sensing the temperature of fluid delivered through a lumen of a housing of the device. A temperature sensor element is isolated from the fluid in the lumen by its reception in an enclosure extending through a portion of the wall of the housing into the lumen. The temperature sensor is provided in association with a connector including suitable leads for transferring the electrically generated signal from the sensor to a cable connected to a computer for use in making thermodilution determinations. By permitting the expensive temperature sensor structure to be reusable without the need for repeated sterilization thereof while permitting the flow-through housing to be disposable, long, troublefree life at low cost is provided.

18 Claims, 3 Drawing Figures

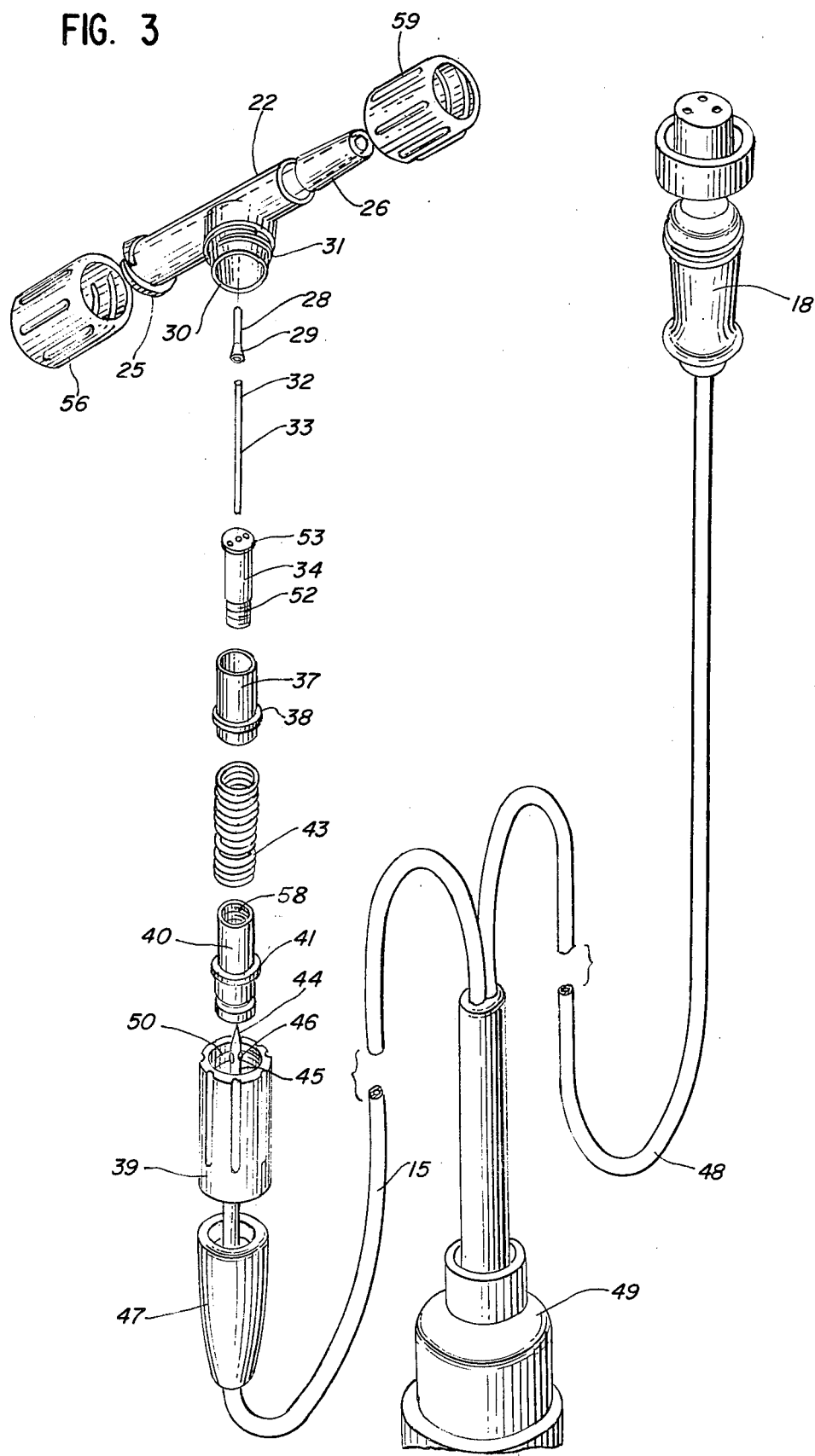

FLUID TEMPERATURE SENSOR

BACKGROUND OF THE INVENTION

1. Field of the Invention

This invention relates to fluid temperature sensors and in particular to sensors for use in determining the temperature of a sterile injectate fluid.

2. Description of the Prior Art

In one known fluid temperature sensor manufactured by Thermometrics Inc., of Edison, N.J., a thermistor temperature sensor is located in the midportion of a clear plastic tube. The thermistor is permanently attached to the device and is electrically isolated from the fluid in the lumen of the tube by means of a thermoplastic protective sleeve. The lead wires from the thermistor are connected to an electrical connector located on the side of the tube. A problem arises in the use of such a temperature sensor in that it is difficult to resterilize the device for use with a second patient. Further, the relatively expensive thermistor must be discarded with the tube in the event the tube becomes damaged.

Another form of mass flowmeter catheter is illustrated in U.S. Pat. No. 3,545,428, of Wilton W. Webster, Jr., to have two concentric lumens, with means coupled to the posterior end of the outer lumen for injecting coolant liquid. A pair of electrical temperature sensing devices is associated with the device.

In U.S. Pat. No. 3,561,266, Michael Auphan et al disclose another device for measuring the flow velocity of a fluid, such as the rate of flow of blood in a human body. The device includes first and second paraxial tubes insertable into the patient's blood vessel for injecting a serum miscible with the blood and for removing a sample of the blood serum mixture respectively. Means are provided for measuring the velocity of the serum and the temperature of the serum, the blood, and the blood serum mixture. An electromagnetic agitator is provided for mixing the blood and the serum.

In U.S. Pat. No. 3,595,079 of Allen R. Grahn, a fluid flow velocity measuring apparatus is disclosed, including a probe having fluid flow velocity and temperature sensor thermistors thereon. The probe is adapted to be inserted into a fluid flow conduit. The device includes circuit means for maintaining the velocity sensor thermistor at a predetermined temperature differential relative to the temperature of the fluid being measured. The probe further includes a flow direction sensor thermistor adjacent the velocity sensor thermistor.

SUMMARY OF THE INVENTION

The present invention comprehends a novel improved injectate temperature sensor having a disposable flow-through housing and a reusable temperature sensing means.

More specifically, the invention comprehends the provision of such an injectate fluid temperature sensor for use in a cardiovascular flow measuring system wherein a cold injectate fluid is delivered in a known amount from a supply through a catheter into a patient's blood vessel and the resultant change in the temperature of the patient's blood vessel is sensed to determine the circulatory blood flow rate.

The improved sensor device includes a disposable housing defining a through lumen for conducting injectate fluid therethrough, a disposable thermally conductive enclosure hermetically sealingly joined to the housing and projecting transversely into said lumen to be in heat transfer association with injectate fluid flowed through the lumen, and a reusable temperature sensor removably installed in the enclosure for providing a signal corresponding accurately to the temperature of the injectate fluid flowed through the lumen.

The temperature sensor is snugly fitted in the enclosure and, in the illustrated embodiment, is potted within a thermally conductive tubular jacket.

The sensor is connected to the end of an electrically conductive cable.

In the illustrated embodiment, the sensor is mounted within a retractable protective cover.

In the illustrated embodiment, the enclosure is formed separately from the housing and is bonded to the housing so as to be hermetically sealed thereto.

The housing, in the illustrated embodiment, defines a threaded connection coaxially of the enclosure and the sensor is provided with a cover having a complementary threaded connection movably connected to the housing connection.

Means are provided for resiliently urging the sensor into the enclosure to have a snug fit therein.

The housing is formed of a low cost material, such as a molded synthetic resin. The enclosure, in the illustrated embodiment, is formed of a low cost material, such as stainless steel.

In the illustrated embodiment, the sensor is mounted in a tube which, in turn, is secured in a base formed of a synthetic resin. The lead wires extend from the sensor through the tube and base.

In the illustrated embodiment, the enclosure extends substantially fully across the lumen of the housing for improved thermal transfer relative to the fluid flowed therepast.

The temperature sensor device of the present invention is extremely simple and economical of construction while yet providing the highly desirable features discussed above.

BRIEF DESCRIPTION OF THE DRAWING

Other features and advantages of the invention will be apparent from the following description taken in connection with the accompanying drawing wherein:

FIG. 3 is an exploded perspective view of the device.

DESCRIPTION OF THE PREFERRED EMBODIMENT

Figure 1:
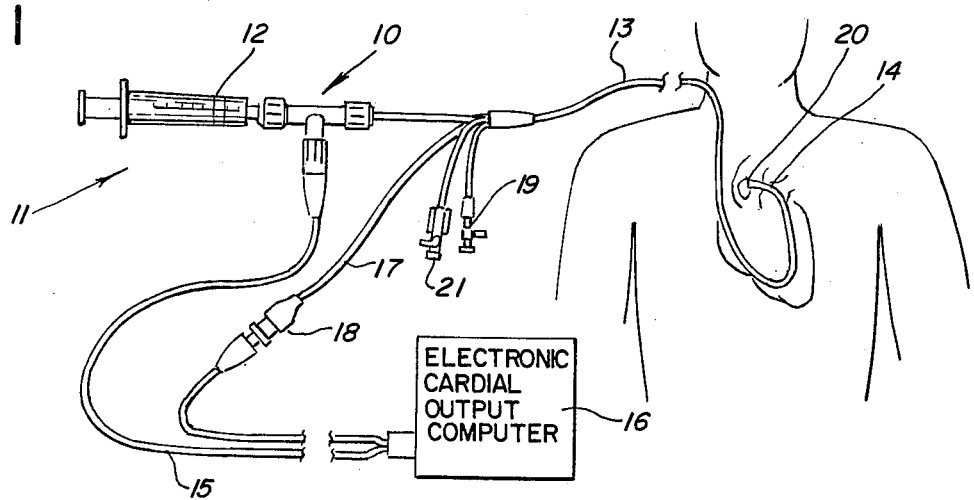
FIG. 1 is a fragmentary elevation illustrating the use of the flow system provided with the fluid temperature sensor device of the invention.

In the illustrative embodiment of the invention as disclosed in the drawing, a fluid temperature sensing device generally designated 10 is shown for use in a flow system generally designated 11 such as a cardiovascular flow measuring system wherein a cold injectate fluid is delivered in a known amount from a supply syringe 12 through a catheter 13 into a patient's blood vessel.

A thermistor temperature sensor 14 is provided in the catheter adjacent the distal end thereof for sensing the temperature of the patient's blood and resultingly, the rate of flow of the blood by means of a thermodilution flow measurement technique.

More specifically, cold injectate fluid is delivered to the catheter 13 through the sensor device 10 which accurately determines the temperature thereof and provides a temperature signal in correspondence therewith through a cable 15 to an electronic cardiac output computer 16 of conventional construction. The blood temperature thermistor 14 is connected through the catheter to a second cable 17 through a suitable connector 18 to the computer 16. The catheter is a multiple lumen catheter with one of the lumens conducting gas from a valved connector 19 for selectively blowing up the catheter balloon 20 at the distal end of the catheter. A second valved connector 21 may be provided for controlling fluid flow through another of the lumens of the catheter, as desired.

In carrying out the thermodilution method of determining blood flow, the cold injectate fluid is delivered in known amount from the syringe 12 through the catheter into the patient's blood stream. A signal corresponding accurately to the temperature of the injectate fluid is determined in the sensor device 10 and fed to the computer. The change in the temperature of the patient's blood stream as sensed by the thermistor 14 is similarly transmitted to the computer which then, on the basis of the change in the patient's blood temperature and the known quantity and temperature of the injectate fluid, determines the total blood flow as a function of volume divided by time. To provide an accurate determination of the blood flow, it is necessary to provide an accurate determination of the temperature of the injectate fluid. The present invention is concerned with an improved form of device for determining the injectate fluid temperature and, more specifically, is concerned with such a device which may utilize a disposable housing 22 of the device 10, and a reusable temperature sensing element 23 separably associated with the housing.

Figure 2:
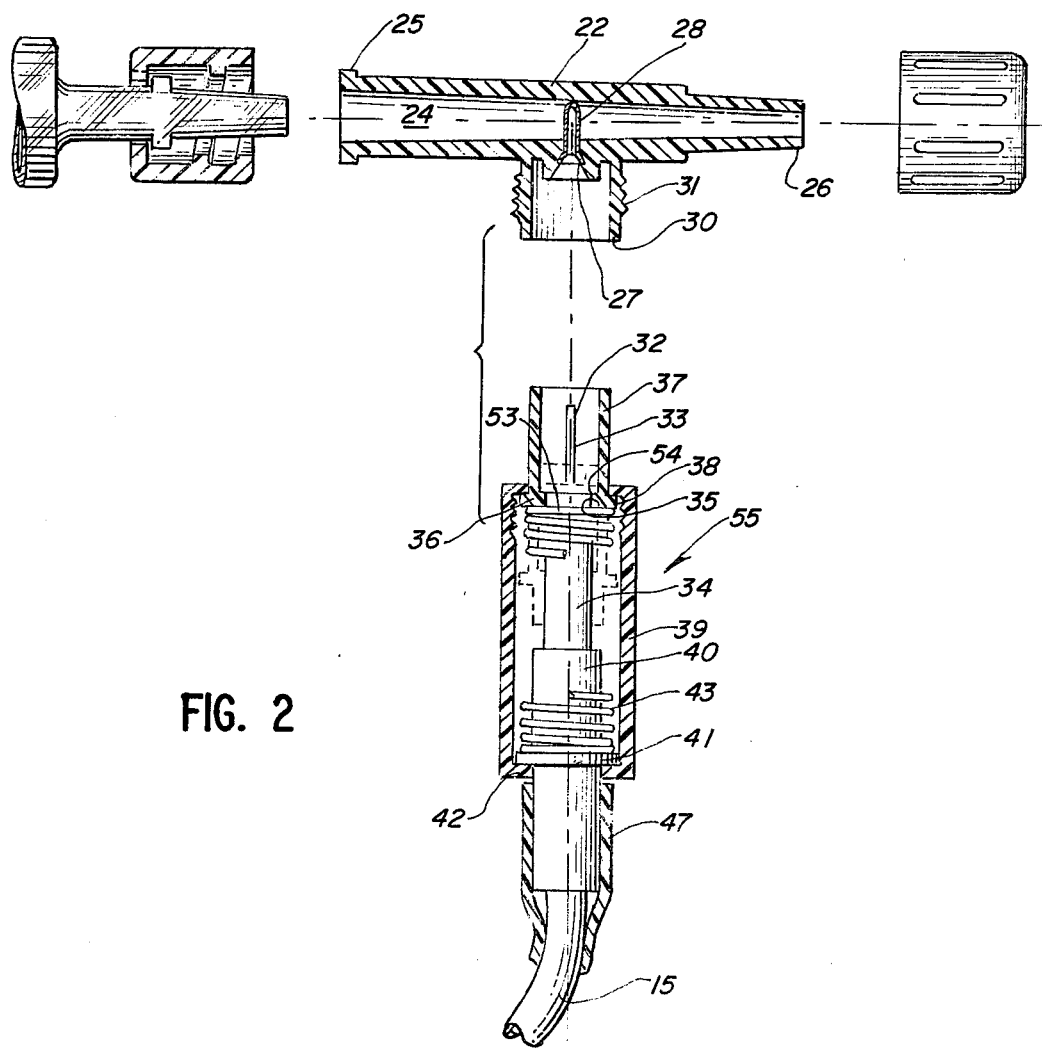
FIG. 2 is a fragmentary exploded diametric section of the temperature sensor device.

More specifically, as illustrated in FIG. 2, housing 22 of the device 10 defines a through lumen 24 having a female luer lock connection 25 at one end and a male luer lock connection 26 at the opposite end.

The body of the housing is provided at a midportion thereof with an opening 27 through which is inserted a thermally conductive enclosure 28. The outer end 29 of the enclosure is hermetically sealed to the housing whereby the enclosure acts as a shield. As seen in FIG. 2, the tubular enclosure may extend substantially fully across the lumen 24.

Coaxially of the lumen, body 22 is provided with an annular wall 30 provided with external threads 31. In the illustrated embodiment, housing 22 is formed of a low cost molded synthetic resin, such as polycarbonate, and the enclosure is formed of a low cost material, such as stainless steel, whereby the assembly of the housing and enclosure is of extremely low cost, permitting the same to be thrown away upon completion of use with a given patient, thereby effectively preventing cross-contamination without the need for resterilization of the sensor device housing.

As further shown in FIG. 2, device 10 includes a thermistor temperature sensor 32 suitable potted in a tubular carrier 33 so as to be received in the enclosure 28. Both the enclosure and tube 33 are formed of thermally conductive material so as to provide facilitated heat transfer between the thermistor and the injectate fluid flowed through the lumen 24.

As best seen in FIG. 3, the probe tube carrier 33 is mounted in a rigid base member 34 extending through an opening 35 in end 36 of a retractable cover 37. The cover is provided with an annular flange 38 which is slidable in an outer cover 39.

A junction element 40 formed of a suitable rigid synthetic resin is provided with an annular collar 41 seated against an end wall 42 of the cover 39 by a coil spring 43 compressed between collar 41 and end wall 36 of cover 37.

The electrical leads 44 from the thermistor 32 extend outwardly through tube 33 to be connected to the conductors 45 of cable 15. In the illustrated embodiment, the wires 44 are lead soldered to the conductors, with the joints covered with shrink sleeves 46.

A strain relief 47 formed of a suitable material such as silicone rubber, is provided at the outer end of cover 39. As further shown in FIG. 3, connector 18 is connected through a cable 48 to an input connector 49 to which cable 15 is also connected for providing the two temperature signals to the computer 16 as discussed above.

As further shown in FIG. 2, cover 39 is provided at its distal end with an internal thread 50 arranged to have threaded engagement with thread 31 of housing wall 30, with cover 37 slidably received within wall 30 and probe tube 33 and thermistor 32 therein snugly fitted in the tubular shield 28. As further shown, the outer end 29 of the shield 28 is frustoconically flared so as to guide the distal end of the tube 33 into the enclosure shield 28.

The thermistor may be potted into the end of the tube with a suitable epoxy potting material, and thus, is in good thermal transfer association through the tube 33 and enclosure 28 with the fluid in the lumen 24 being delivered therethrough from the syringe 12.

As further shown in FIG. 3, base member 34 is provided with a male threaded end 52 of junction element 40. Base member 34 is provided with a distal collar 53 which, as seen in FIG. 2, engages an inturned annular flange 54 of cover 37 radially inwardly of flange 38. Thus, the threaded connection of base member portion 52 with a threaded portion 58 of junction element 40 secures the assembly of the base member 34, cover 37, spring 43, and junction element 40, while permitting the cover 37 to be resiliently retracted into cover 39 against the biasing action of spring 43 when the connector assembly generally designated 55 is connected to the threaded wall 30 of housing 22.

In use, the injectate fluid is delivered through lumen 24 of the sensing device 10 by suitable manipulation of syringe 12. The fluid is preferably at a temperature of between zero and 25° C. so as to provide a positive thermodilution reading when mixed with the patient's blood as sensed by thermistor 14. The temperature of the injectate fluid as it passes through lumen 24 is accurately determined by the sensor 32, whereby the temperature signals delivered from sensors 32 and 14 may be used in computer 16 for providing the desired blood flow rate information.

As housing 22 and enclosure 28 are low cost disposable items and the enclosure 28 acts as a biological shield between the fluid in lumen 24 and connector 55, there is no need for maintaining the connector 55 sterile. Thus, the connector 55, and more specifically, the sensor 32, may be reused repeatedly with different sensor devices 11 as with different patients without possibility of cross-contamination and infection.

The provision of the resiliently extensible cover portin 37 protects the sensor probe when the connector 55 is disconnected from housing 22.

In the illustrated embodiment, enclosure shield 28 comprises a separate element bonded to the housing. As will be obvious to those skilled in the art, however, the enclosure 28 may be formed as an integrally molded part of housing 22, as desired.

Further, the device 11 is shown as a separate device from the catheter to be removably connected thereto by suitable luer nuts 56 and 59 cooperating with the female luer lock 25 and male luer lock 26, respectively.

While the novel device 10 has been illustrated in connection with a thermodilution cardiac output measurement system, as will be obvious to those skilled in the art, the device may be utilized as a low cost disposable fluid temperature sensing device generally.

As discussed above, the housing 22 is preferably formed of a transparent synthetic resin, such as polycarbonate, to permit observation of the fluid flowed therethrough as during flushing so as to detect bubbles and the like. The housing and installed enclosure 28 may be effectively sterilized as by ETO gas sterilization and suitably packaged for sterile use as desired.

As will be obvious to those skilled in the art, the base member 34 and junction element 40 may alternatively be formed as an integral one-piece structure. Further alternatively, a suitable retaining clip (not shown) may be substituted for flange 53 within the scope of the invention.

Junction element 40 may further be alternatively provided with an annular undercut (not shown) for snapped engagement with outer cover 39, thereby eliminating the need for strain relief 47.

Further alterntively, sensor 32 may be cast in a cylindrical form of thermally conductive, electrically insulative synthetic resin, such as epoxy resin, permitting elimination of carrier 33, within the scope of the invention.

The foregoing disclosure of specific embodiments is illustrative of the broad inventive concepts comprehended by the invention.

I claim:

1. For use in a flow system such as a cardiovascular flow measuring system wherein a cold injectate fluid is delivered in a known amount from a supply through a catheter into a patient's blood vessel and the resultant change in the temperature of the patient's blood is sensed to determine the circulatory blood flow rate, an improved injectate fluid temperature sensor comprising:
   a disposable housing defining a through lumen for conducting injectate fluid therethrough;
   a disposable thermally conductive enclosure hermetically sealingly joined to the housing and projecting transversely into said lumen to be in heat transfer association with injectate fluid conducted through said lumen; and
   a reusable temperature sensor removably installed in said enclosure, said sensor providing a signal corresponding accurately to the temperature of the injectate fluid conducted through said lumen.

2. The temperature sensor of claim 1 wherein the sensor is snugly fitted in the enclosure.

3. The temperature sensor of claim 1 wherein said sensor is potted within a thermally conductive jacket.

4. The temperature sensor of claim 1 wherein said sensor is potted within a thermally conductive jacket carried on the end of an electrically conductive cable, said cable transmitting the sensed temperature signal.

5. The temperature sensor of claim 1 further including a retractable protective cover surrounding the temperature sensor, said cover protecting the sensor when separated from the enclosure.

6. The temperature sensor of claim 1 wherein said enclosure is bonded to the housing.

7. The temperature sensor of claim 1 wherein said enclosure comprises a separately formed element secured to said housing.

8. The temperature sensor of claim 1 wherein said housing defines a threaded connector coaxially of said enclosure and said sensor is provided in a cover having a threaded connector removably connected to said housing threaded connector.

9. The temperature sensor of claim 1 including means for resiliently urging the sensor into said enclosure.

10. The temperature sensor of claim 1 wherein said sensor has an external configuration complementary to said enclosure and is resiliently urged into a snug fit therein.

11. The temperature sensor of claim 1 wherein said housing is formed of a molded synthetic resin.

12. The temperature sensor of claim 1 wherein said enclosure is formed of stainless steel.

13. The temperature sensor of claim 1 wherein said sensor is mounted in a probe tube.

14. The temperature sensor of claim 1 wherein said sensor is mounted in a probe tube secured in a support base formed of a synthetic resin.

15. The temperature sensor of claim 1 wherein said sensor is mounted in a probe tube, lead wires being connected to said sensor and extending outwardly through said probe tube for connection to an electrical conductor cable.

16. The temperature sensor of claim 1 wherein said sensor comprises a thermistor.

17. The temperature sensor of claim 1 wherein said sensor is disposed in a probe tube and a retractable cover is yieldably disposed about the probe tube.

18. The temperature sensor of claim 1 wherein said enclosure extends substantially fully across said lumen.

* * * * *

Adverse Decisions In Interference

Patent No. 4,476,877, John M. Barker, FLUID TEMPERATURE SENSOR, Interference No. 103,146, final judgment adverse to the patentees rendered June 29, 1999, as to claims 1-18.
*(Official Gazette June 13, 2000)*

Adverse Decisions In Interference

Patent No. 4,476,877, John M. Barker, FLUID TEMPERATURE SENSOR, Interference No. 103,146, final judgment adverse to the patentees rendered June 29, 1999, as to claims 1-18.
*(Official Gazette July 4, 2000)*

Adverse Decision in Interference

Patent No. 4,476,877, John M. Barker, FLUID TEMPERATURE SENSOR, Interference No. 103,146, final judgment adverse to the patentee rendered June 29, 1999, as to claims 1-18.
*(Official Gazette November 28, 2000)*